US005260020A

United States Patent [19]
Wilk et al.

[11] Patent Number: 5,260,020
[45] Date of Patent: Nov. 9, 1993

[54] METHOD AND APPARATUS FOR CATHETER STERILIZATION

[76] Inventors: Peter J. Wilk, 185 West End Ave., New York, N.Y. 10023; Jonathan Tiefenbrun, 62 Country Rd., Mamaroneck, N.Y. 10543

[21] Appl. No.: 946,550

[22] Filed: Sep. 17, 1992

[51] Int. Cl.⁵ ............................ A61L 2/08; A61N 5/00
[52] U.S. Cl. ................................ 422/22; 422/24; 604/21; 604/267; 606/15; 606/29; 606/33; 219/10.55 R; 607/122
[58] Field of Search ...................... 422/20, 22, 24, 294, 422/307, 28, 292; 604/21, 265, 266, 267; 128/786; 219/10.55 R; 220/87.1; 250/455.11; 606/15, 29, 33

[56] References Cited

U.S. PATENT DOCUMENTS

| | | | |
|---|---|---|---|
| 4,448,198 | 5/1984 | Turner | 128/422 |
| 4,712,559 | 12/1987 | Turner | 128/422 |
| 4,886,505 | 12/1989 | Haynes et al. | 604/265 |
| 4,906,238 | 3/1990 | Greenfeld et al. | 604/265 X |
| 5,029,585 | 7/1991 | Lieber et al. | 128/786 X |

Primary Examiner—Robert J. Warden
Assistant Examiner—E. Leigh Dawson
Attorney, Agent, or Firm—R. Neil Sudol; Henry D. Coleman

[57] ABSTRACT

Techniques for effectively sterilizing catheters, particularly long-dwelling intravenous catheters, are disclosed. The techniques include the transmission and dispersion of ultraviolet or infrared radiation, the heating or cooling of a catheter distal end portion, and the transmission of electrical current along the catheter and through the catheter lumen or organic tissues in which the catheter resides.

25 Claims, 2 Drawing Sheets

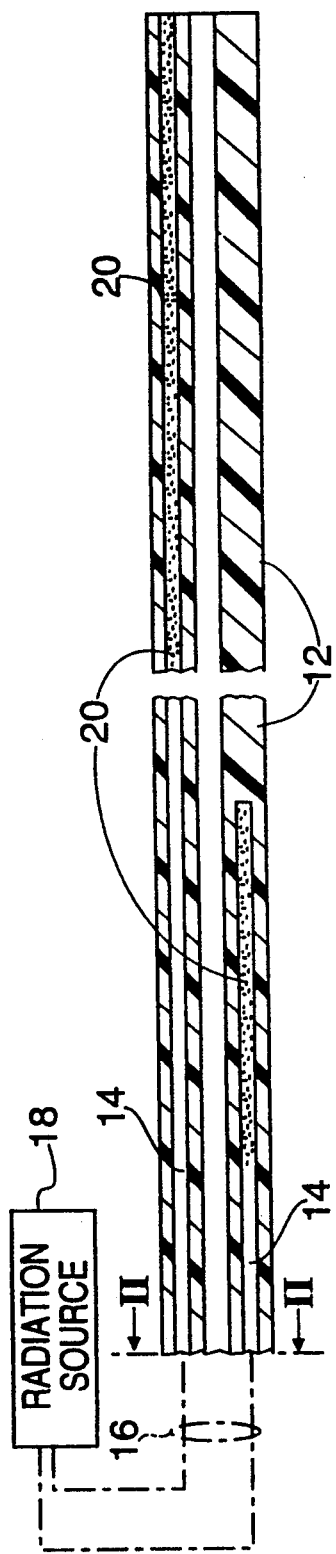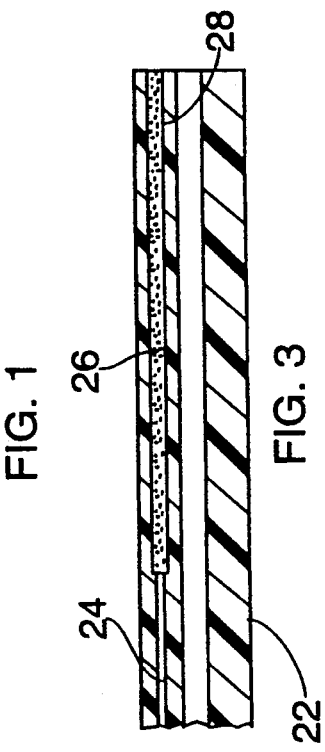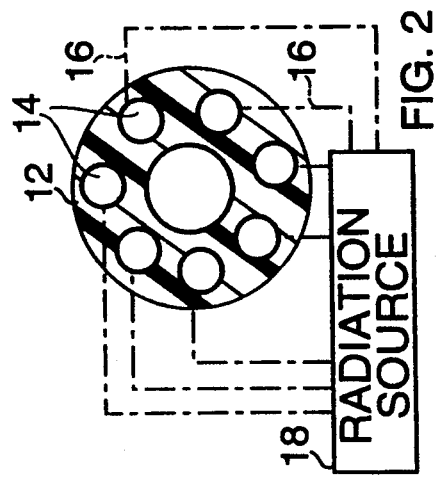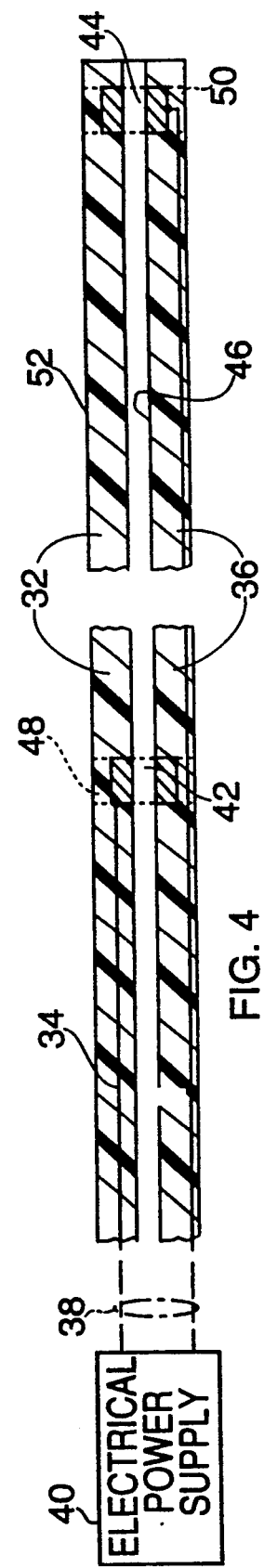

METHOD AND APPARATUS FOR CATHETER STERILIZATION

BACKGROUND OF THE INVENTION

This invention relates to a method for effectively sterilizing catheters, particularly including, but not limited to, intravenous catheters. This invention also relates to associated catheter assemblies with sterilization componentry incorporated therein.

A problem of long-dwelling catheters is fungal sepsis. Of long-dwelling catheters, approximately ten percent become septic. A significant number of those will result in death.

OBJECTS OF THE INVENTION

An object of the present invention is to provide a method for at least partially sterilizing catheters.

Another object of the present invention is to provide a method for reducing fungal sepsis.

Another, more particular, object of the present invention is to provide a method for at least partially sterilizing long-dwelling catheters while the catheters are inserted intravenously.

A further object of the present invention is to provide a related device or assembly for use in maintaining sterility of a long-dwelling catheter.

These and other objects of the present invention will be apparent from the drawings and detailed descriptions herein.

SUMMARY OF THE INVENTION

A catheter assembly comprises, in accordance with one embodiment of the present invention, a catheter, an optical fiber connected to the catheter and extending longitudinally along at least a segment of the catheter, a connector for coupling the optical fiber at an input end to a source of sterilizing radiation, and a dispersion component connected to the catheter and disposed at least at a distal end of the optical fiber for dispersing radiation from the source along a portion of the catheter to at least partially sterilize the catheter along that portion.

Pursuant to another feature of the present invention, the optical fiber is one of a plurality of optical fibers extending along the segment of the catheter. The optical fibers may terminate at different points along the catheter, thereby facilitating sterilization of a greater length of catheter.

Pursuant to a further feature of the present invention, the optical fiber is embedded at least partially in the catheter along the catheter segment.

Pursuant to an additional feature of the present invention, the optical fiber is adapted to transmit ultraviolet radiation and the dispersion component is adapted to disperse ultraviolet radiation. Pursuant to an alternative feature of the present invention, the optical fiber is adapted to transmit infrared radiation and the dispersion component is adapted to disperse infrared radiation.

The dispersion component may take the form of a roughened section of the optical fiber. Alternatively, the portion of the catheter to be sterilized by the incoming radiation may be formed with irregularities in micro-structure which cause electromagnetic wave dispersion within a predetermined range of wavelengths.

A catheter assembly comprises, in accordance with another embodiment of the present invention, a catheter, a heat conductive conductor connected to the catheter and extending longitudinally along at least a segment of the catheter, and a connector for connecting the conductor at an input end to an external heat exchanger. The conductor is disposed in such relation to the catheter that heat is exchanged between the conductor and the catheter along the portion thereof to be sterilized. In a specific realization of the invention, a heat exchange component is disposed along the catheter and is connected to the conductor for exchanging heat energy with the catheter along a portion thereof to at least partially sterilize the catheter along that portion. The conductor may be at least partially embedded in the catheter.

The direction of heat conduction may either be into the catheter, for effective sterilization by a temperature elevation, or out of the catheter, for sterilization by a temperature drop.

A catheter assembly comprises, in accordance with a further embodiment of the present invention, a catheter, an electrical conductor connected to the catheter and extending longitudinally along at least a segment of the catheter, a connector for linking the conductor at an input end to a source of electrical power, and sterilization componentry connected to the conductor and the catheter and disposed at a predetermined portion of the catheter for using electrical current conducted by the conductor from the source to at least partially sterilize the catheter along that portion.

Pursuant to another feature of the present invention, the sterilization componentry includes a resistive heat generating element disposed along the conductor (for example, along a distal end portion thereof) for increasing the temperature of the portion relative to an ambient temperature level. Of course, a resistive conductor may be provided along the length of the catheter and along intravenous tubing which connects the catheter at an input or upstream end to an intravenous supply, thereby enhancing the sterility of the intravenous line.

Where the conductor is one of a pair of conductors and the sterilization componentry includes a pair of terminals connected to respective ones of the conductors, the terminals may be adapted to contact organic tissues upon insertion of the catheter in an organ of a patient and to induce the conduction of an electrical current through the tissues to at least incapacitate microorganisms harbored in the tissues. Alternatively or additionally, the terminals are disposed along a lumen of the catheter for transmitting an electrical current through a portion of the lumen to thereby sterilize the same. The current may, of course, be conducted along the entire catheter in accordance with the present invention.

A method for effectively sterilizing a catheter comprises, in accordance with an embodiment of the present invention, the steps of (a) generating electromagnetic radiation having a wavelength adapted to at least incapacitate microorganisms of a predetermined variety, (b) conducting the radiation along an optical fiber connected to the catheter, and (c) dispersing the radiation along a portion of the catheter to bathe that portion in the radiation.

The wavelength of the radiation may be, for example, in the ultraviolet or infrared portion of the electromagnetic spectrum. The radiation may be conducted along a plurality of optical fibers in the catheter.

A method for effectively sterilizing a catheter comprises, in accordance with another embodiment of the present invention the steps of (i) connecting the catheter to an external heat exchange device, (ii) conducting heat energy through a conductor extending between a predetermined portion of the catheter and the heat exchange device, and (iii) transferring sufficient heat energy between the conductor and the catheter along the predetermined portion thereof to change a temperature of that portion to a magnitude adapted to at least incapacitate microorganisms of a predetermined variety.

In accordance with a specific application of this embodiment of the invention, the heat exchange device is a heat source and the step of conducting heat energy includes the step of conducting heat energy from the heat source to the predetermined portion of the catheter. Then, the step of transferring includes the step of transferring sufficient heat energy from the conductor into the catheter along the predetermined portion thereof to elevate a temperature of that portion to a magnitude adapted to at least incapacitate microorganisms of the predetermined variety.

In accordance with an alternative specific application of this embodiment of the invention, the heat exchange device is a heat sink and the step of conducting heat energy includes the step of conducting heat energy to the heat source from the predetermined portion of the catheter. In that case, the step of transferring heat energy includes the step of transferring sufficient heat energy into the conductor from the catheter along the predetermined portion thereof to lower a temperature of that portion to a magnitude adapted to at least incapacitate microorganisms of the predetermined variety.

In accordance with another feature of the present invention, the step of transferring continues for a predetermined duration, whereupon the steps of conducting and transferring are terminated.

A method for effectively sterilizing a catheter comprises, in accordance with yet another embodiment of the present invention, the steps of (1) connecting the catheter to an external electrical power supply, (2) conducting electrical energy through a conductor extending between a predetermined portion of the catheter and the power supply, and (3) using electrical current conducted by the conductor from the source to at least partially sterilize the catheter along the predetermined portion.

According to another feature of the present invention, the step of using electrical current includes the steps of converting the electrical current to heat energy and transferring sufficient heat energy from the conductor into the catheter along the predetermined portion thereof to elevate a temperature of that portion to a magnitude adapted to at least incapacitate microorganisms of a predetermined variety.

Alternatively, the step of using electrical current includes the steps of conducting the electrical current along an outer surface of the catheter and through organic tissues located along the outer surface, to at least incapacitate microorganisms harbored in the tissues. In another alternative embodiment of this method, electrical current is conducted through the lumen of the catheter to effectively sterilize the lumen.

A method in accordance with the present invention serves to reduce fungal sepsis. Accordingly, the incidence of deaths resulting from fungal sepsis is reduced.

A method serves in the sterilization of long-dwelling catheters while the catheters are inserted intravenously. Hospital personnel may periodically connect long-dwelling catheters to, for example, ultraviolet radiation sources. Alternatively, the catheters may be continuously connected to a source of heat energy or electrical energy for maintaining the temperature of the in-dwelling portion of the catheter at a temperture which is sufficiently elevated to inhibit or prevent the proliferation and growth of a predetermined kind of microorganism, such as the microorganism(s) responsible for fungal sepsis.

BRIEF DESCRIPTION OF THE DRAWINGS

FIG. 1 is a partial longitudinal cross-sectional view, on an enlarged scale, of a long-dwelling catheter assembly in accordance with the present invention.

FIG. 2 is a traverse cross-sectional view taken along line II—II in FIG. 1.

FIG. 3 is a partial longitudinal cross-sectional view, on an enlarged scale, of another long-dwelling catheter assembly in accordance with the present invention.

FIG. 4 is a partial longitudinal cross-sectional view, on an enlarged scale, of a further long-dwelling catheter assembly in accordance with the present invention.

DETAILED DESCRIPTION

Figure 5:
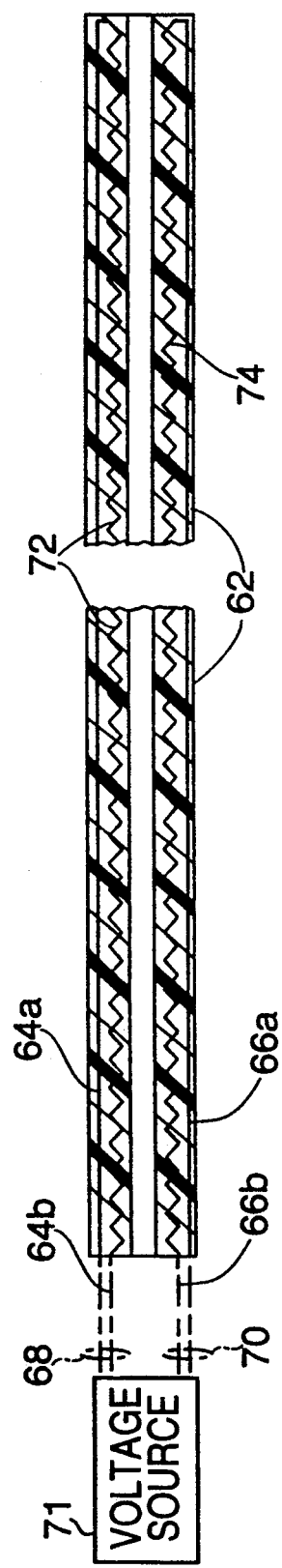
FIG. 5 is a partial longitudinal cross-sectional view, on an enlarged scale, of an additional long-dwelling catheter assembly in accordance with the present invention.

As illustrated in FIG. 1, a long-dwelling catheter assembly comprises a catheter 12 and a plurality of optical fibers 14 embedded in the catheter and extending longitudinally along at least a segment of the catheter. Optical fibers 14 transmit electromagnetic radiation within a predetermined range of wavelengths, for example, in the ultraviolet or infrared portions of the spectrum and are coupled at proximal ends via a schematically represented connector 16 to a source 18 of ulraviolet or infrared radiation.

The radiation produced by source 18 and carried by fibers 14 includes radiation of a wavelength which is predetermined to be effective in inhibiting growth of a selected kind of microorganism, for example, a fungus or a bacterium which characteristically inhabits long-dwelling catheters.

Along a terminal segment 20, each fiber 14 is provided with a roughened surface which disperses in a cylindrical dispersion pattern incoming radiation of the predetermined frequency generated by source 18. In at least some long-dwelling catheters, a single optical fiber having a roughened outer surface may be sufficient for effective sterilization of the catheter 12 along a preselected portion thereof inserted into a patient, namely, that distal endportion of the catheter which is coextensive with the roughened portion of the radiation transmitting fiber. More specifically, the sterilizing radiation dispersed by roughened terminal segments 20 of optical fibers 14 is emitted through a cylindrical external surface of catheter 12 which is in contact with the patient's tissues. Thus, the dispersion pattern generated by roughened segments 20 is substantially coextensive with a portion of the cylindrical external surface of catheter 12.

As depicted schematically in FIG. 1, optical fibers 14 terminate at different points along catheter 12 and accordingly have roughened distal segments 20 which are coextensive with different portions of catheter 12. In this way, essentially the entire length of catheter 12 may be bathed in sterilizing radiation.

Generally, it is contemplated that source 18 will be periodically connected to fibers 14 of catheter 12 for predetermined intervals. The intervals are of sufficient periodicity and sufficient duration to effectively sterilize catheter 12 of the preselected kind of microorganism. Accordingly, the incidence of sepsis will be decreased and the catheter 12 can remain implanted in the patient for a longer time.

FIG. 3 illustrates a modified embodiment wherein a catheter 22 to be sterilized by incoming radiation is formed at the distal end of each optical fiber 24 with irregularities 26 in micro-structure which cause electromagnetic wave dispersion within a predetermined range of wavelengths. The microscopic irregularities 26 may take the form of a transparent flexible material stuffed into cavities 28 formed at the distal ends of fibers 24.

As shown in FIG. 4, another long-dwelling catheter assembly comprises a catheter 32 traversed longitudinally by a pair of embedded electrical conductors 34 and 36. A schematically represented connector 38 serves to link conductors 34 and 36 at an input end to a source or supply 40 of electrical power. Catheter 32 is provided with sterilization components in the form of two annular terminals or contacts 42 and 44 connected to respective conductors 34 and 36 and embedded in catheter 32.

Terminals 42 and 44 may be disposed solely along an inner surface or lumen 46 of catheter 32. Alternatively, terminals 48 and 50 may be provided along an outer surface 52 of catheter 32. In the former case, energization of conductors or leads 34 and 36 by supply 40 induces electrical current to flow in a substantially cylindrical path through fluid present in catheter lumen 46. The electrical current serves to destroy or incapacitate microorganisms harbored within lumen 46. In the latter case, energization of conductors or leads 34 and 36 by supply 40 induces electrical current to flow in a substantially cylindrical path longitudinally along the outer surface of the catheter and possibly through organic tissues into which catheter 32 is inserted, thereby at least incapacitating microorganisms harbored in the tissues.

As discussed hereinabove with reference to FIGS. 1-3, the sterilization of long-dwelling catheter 32 is implemented by periodically connecting conductors 34 and 36 to supply 40 for intervals of predetermined durations. During such sterilization operations, it may be necessary to flush catheter 32 with a saline solution for ensuring adequate electrical current conduction.

It is to be noted that a plurality of terminal pairs (not shown) may be provided to conduct current along staggered portions of catheter 32. In the event that only a distal end portion of the catheter, for example, is subject to microorganism infestation, then only portions of the catheter at the distal end thereof need be sterilized.

As depicted in FIG. 5, yet another long-dwelling catheter assembly comprises a catheter 62 traversed longitudinally by two pairs of embedded electrical conductors 64a, 64b and 66a, 66b. Schematically represented connectors 68 and 70 serve to link conductors 64a, 64b and 66a, 66b at input ends to a voltage or current source 71. Catheter 62 is provided with sterilization components in the form of a pair of schematically represented resistive heat-generating elements 72 and 74 embedded in a portion of catheter 62 for increasing the temperature of that portion relative to an ambient temperature level. Of course, a resistive conductor (not shown) may be provided along intravenous tubing (not shown) which connects catheter 62 at an input or upstream end to an intravenous supply (not shown), thereby enhancing the sterility of the intravenous line.

Figure 6:
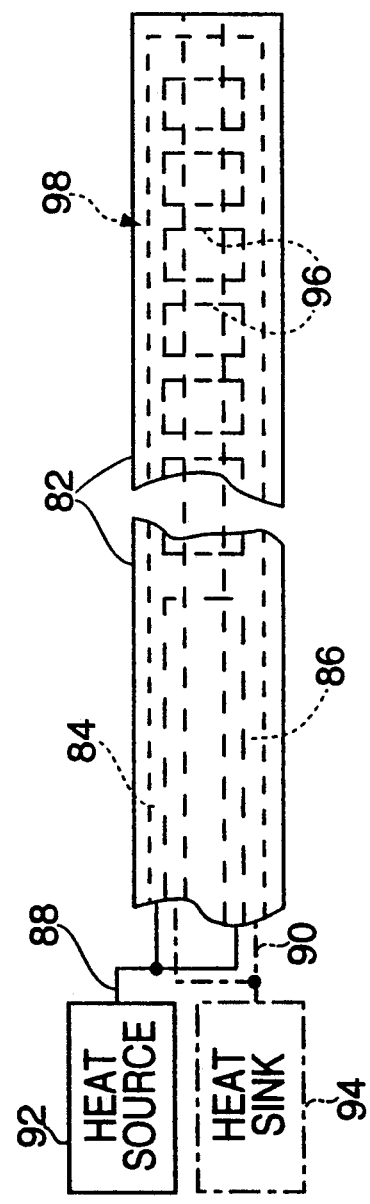
FIG. 6 a partial side elevational view, on an enlarged scale, of yet another long-dwelling catheter assembly in accordance with the present invention.

A catheter assembly as shown in FIG. 6 comprises a catheter 82, one or more heat conductive conductors 84 and 86 connected to catheter 82 and embedded longitudinally in at least a segment of the catheter. A schematically illustrated connector 88 or 90 serves to connect conductors 84 and 86 at a proximal or input end to an external heat exchanger in the form of a heat source 92 or, alternatively, a heat sink 94. Conductors 84 and 86 are provided at a distal end with a plurality of annular webs 96 which serve as heating or cooling fins of a heat exchanger 98 at the distal end of conductors 84 and 86.

It is to be noted that a plurality of heat exchange components such as heat exchanger 98 may be provided along the length of catheter 82, each such heat exchanger being serviced by a respective heat conductive rod or a plurality of such heat conductors.

Accordingly, conductors 84 and 86 are disposed in such relation to catheter 82 (via heat exchanger 98) that heat is exchanged between conductors 84 and 86 and catheter 82 along the portion thereof to be sterilized. The direction of heat conduction is into catheter 82 in the event that heat source 92 is connected to heat exchanger 98 via conductors or rods 84 and 86. Alternatively, the direction of heat conduction is out of catheter 82 in the event that conductors 84 and 86 are connected at their proximal ends to heat sink 94.

The amount of heat energy transferred between conductors 84 and 86 and catheter 82 along a predetermined portion thereof changes a temperature of that catheter portion to a magnitude adapted to at least incapacitate microorganisms of a predetermined variety.

As described herein with reference to other embodiments of a sterilizing catheter assembly, heat source 92 or heat sink 94 may be connected to catheter 82 periodically for predetermined durations in order to effectively sterilize the desired portion(s) of catheter 82 of microorganisms.

Although the invention has been described in terms of particular embodiments and applications, one of ordinary skill in the art, in light of this teaching, can generate additional embodiments and modifications without departing from the spirit of or exceeding the scope of the claimed invention. It is to be noted, for example, that one or more of the methods and devices disclosed herein may be used in combination with one another, either simultaneously or in succession, in order to sterilize a long-dwelling catheter. The techniques may also be used with other, known methods, such as ultrasonic sterilization.

Accordingly, it is to be understood that the drawings and descriptions herein are proffered by way of example to facilitate comprehension of the invention and should not be construed to limit the scope thereof.

What is claimed is:

1. A catheter assembly comprising:
   a catheter with a distal end portion for insertion into a patient, said distal end portion being defined in part by an external surface which comes into contact with internal tissues of the patient upon insertion of said distal end portion into the patient;
   optical transmission means including an optical fiber connected to said catheter and extending longitudinally along at least a segment of said catheter for transmitting electromagnetic sterilizing radiation to said distal end portion of said catheter;

connector means for connecting said optical fiber at an input end to a source of said sterilizing radiation; and dispersion means connected to said catheter and disposed at least at a distal end of said optical fiber for dispersing electromagnetic radiation from said source outwardly through said external surface in a cylindrical dispersion pattern to bathe said catheter with said radiation along said distal end portion.

2. The assembly defined in claim 1 wherein said optical fiber is one of plurality of optical fibers extending along said segment of said catheter.

3. The assembly defined in claim 2 wherein said optical fibers terminate at different points along said catheter.

4. The assembly defined in claim 1 wherein said optical fiber is embedded in said catheter along said segment.

5. The assembly defined in claim 1 wherein said sterilizing radiation is ultraviolet radiation.

6. The assembly defined in claim 1 wherein said sterilizing radiation is infrared radiation.

7. A catheter assembly comprising:
a catheter having a distal end portion insertable into a patient;
a heat conductor connected to said catheter and extending longitudinally along at least a segment of said catheter to said distal end portion;
connector means for connecting said heat conductor at an input end to an external heat exchanger; and
heat exchanger means connected to said heat conductor and disposed at said distal end portion of said catheter for exchanging heat energy with said catheter along said distal end portion of said catheter to at least partially sterilize said catheter along said distal end portion.

8. The assembly defined in claim 7 wherein said conductor is at least partially embedded in said catheter.

9. A catheter assembly comprising:
a catheter with a distal end portion for insertion into a patient, said distal end portion being defined in part by a surface which comes into contact with internal tissues of the patient upon insertion of said distal end portion into the patient;
transmission means connected to said catheter and extending longitudinally along at least a segment of said catheter for carrying electrical current to said segment;
connector means for connecting said transmission means at an input end to a source of electrical power; and
sterilization means connected to said transmission means and said catheter for conducting electrical current from said transmission means longitudinally along said surface of said catheter in an essentially cylindrical path to at least partially sterilize said catheter along said distal end portion, said sterilization means including a pair of terminals connected to said transmission means, said terminals being spaced from one another along said catheter.

10. The assembly defined in claim 9 wherein said terminals are disposed along a lumen of said catheter.

11. The assembly defined in claim 9 wherein said terminals are disposed along an outer surface of said catheter, whereby said terminals contact organic tissues upon insertion of said catheter in an organ of a patient and to induce the conduction of an electrical current through said tissues to at least incapacitate microorganisms harbored in said tissues.

12. A catheter assembly comprising:
a catheter;
transmission means connected to said catheter and extending longitudinally along at least a segment of said catheter for carrying electrical current to said segment;
connector means for connecting said transmission means at an input end to a source of electrical power; and
resistive heat generating means operatively connected to said transmission means for converting transmitted electrical current into heat energy to increase the temperature of an inserted portion of said catheter relative to an ambient temperature level.

13. A method for effectively sterilizing a catheter, comprising the steps of:
providing a catheter;
generating electromagnetic radiation for at least incapacitating microorganisms of a predetermined variety;
conducting said electromagnetic radiation along an optical fiber connected to said catheter; and
dispersing said electromagnetic radiation in a cylindrical dispersion pattern outwardly through an inserted portion of said catheter to bathe said inserted portion in said electromagnetic radiation.

14. The method defined in claim 13 wherein said wavelength is in the ultraviolet portion of the electromagnetic spectrum.

15. The method defined in claim 13 wherein said wavelength is in the infrared portion of the electromagnetic spectrum.

16. The method defined in claim 13 wherein said radiation is conducted along a plurality of optical fibers in said catheter.

17. A method for effectively sterilizing a catheter, comprising the steps of:
providing a catheter;
connecting said catheter to an external heat exchange device;
conducting heat energy through a conductor extending between a portion of said catheter and said heat exchange device; and
transferring sufficient heat energy between said conductor and said catheter along said portion thereof to change a temperature of said portion to a magnitude for at least incapacitating microorganisms of a predetermined variety.

18. The method defined in claim 17 wherein said heat exchange device is a heat source, said step of conducting including the step of conducting heat energy from said heat source to said portion of said catheter, said step of transferring including the step of transferring sufficient heat energy from said conductor into said catheter along said portion thereof to elevate a temperature of said portion to a magnetic for at least incapacitating microorganisms of said predetermined variety.

19. The method defined in claim 18 wherein said step of transferring continues for a predetermined duration, whereupon said steps of conducting and transferring are terminated.

20. The method defined in claim 17 wherein said heat exchange device is a heat sink, said step of conducting including the step of conducting heat energy to said heat source from said portion of said catheter, said step of transferring including the step of transferring sufficient heat energy into said conductor from said catheter along said portion thereof to lower a temperature of said portion to a magnitude for at least incapacitating microorganisms of said predetermined variety.

21. The method defined in claim 20 wherein said step of transferring continues for a predetermined duration, whereupon said steps of conducting and transferring are terminated.

22. A method for effectively sterilizing a catheter, comprising the steps of:
providing a catheter with a distal end portion for insertion into a patient, said distal end portion being defined in part by a surface which comes into contact with internal tissues of the patient upon insertion of said distal end portion into the patient, said catheter being provided with transmission means connected to said catheter and extending longitudinally along at least a segment of said catheter for carrying electrical current to said segment, said catheter being provided further with two terminals connected to said transmission means and spaced from one another along said surface;
connecting said transmission means to an external electrical power supply;
conducting electrical energy through said electrical conductor from said power supply; and
transmitting electrical current from said electrical conductor longitudinally along said surface in a substantially cylindrical path between said two terminals to at least partially sterilize said catheter along said surface.

23. A method for effectively sterilizing a catheter, comprising the steps of:
providing a catheter having an electrical conductor and a resistive element connected to said conductor and disposed in a distal end portion of said catheter;
providing an external electrical power supply;
connecting said conductor to said external electrical power supply;
conducting electrical current from said power supply through said conductor; and
converting electrical current conducted through said conductor to heat energy in said resistive element and transferring sufficient heat energy from said resistive element into said catheter along said distal end portion thereto to elevate a temperature of said distal end portion to a magnitude for at least incapacitating microorganisms of a predetermined variety.

24. The method defined in claim 22 wherein said step of transmitting includes the steps of transmitting said electrical current along an outer surface of said catheter and through organic tissues located along said outer surface, to at least incapacitate microorganisms harbored in said tissues.

25. The method defined in claim 22 wherein said step of transmitting includes the step of transmitting said electrical current through a lumen of said catheter to at least incapacitate microorganisms harbored in said lumen.

* * * * *